United States Patent
Roof et al.

(10) Patent No.: US 7,312,065 B2
(45) Date of Patent: Dec. 25, 2007

(54) LAWSONIA INTRACELLULARIS OF EUROPEAN ORIGIN AND VACCINES, DIAGNOSTIC AGENTS AND METHODS OF USE THEREOF

(75) Inventors: Michael B. Roof, Ames, IA (US);
Jeremy J. Kroll, Urbandale, IA (US);
Jeffrey P. Knittel, Melbourne, FL (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 267 days.

(21) Appl. No.: 10/891,745

(22) Filed: Jul. 15, 2004

(65) Prior Publication Data

US 2005/0031647 A1   Feb. 10, 2005

Related U.S. Application Data

(60) Provisional application No. 60/490,001, filed on Jul. 25, 2003.

(51) Int. Cl.
*C12N 1/12* (2006.01)

(52) U.S. Cl. .................. 435/252.1; 435/243; 435/366; 435/383; 435/395; 435/403; 424/93.4; 424/234.1; 424/825

(58) Field of Classification Search ................ 435/243, 435/252.1, 366, 383, 395, 403; 424/93.4, 424/234.1, 825
See application file for complete search history.

(56) References Cited

U.S. PATENT DOCUMENTS 5,714,375 A   2/1998   Knittel et al.
5,885,823 A   3/1999   Knittel et al.

OTHER PUBLICATIONS

NIH Guide, vol. 22, No. 28, Multicomponent Vaccine Development, Aug. 6, 1993.*
Fattom et al. Vaccine vol. 17, No. 2, Jan. 1999, pp. 126-133.*
Abstract of the General Meetings No. 101 May 23, 2001: Session No. 263/Z Abstract Z-40; Efficacy of an Avirulent *Lawsonia intracellularis* Vaccine in Swine; J.J. Kroll et al.
International Search Report Reference No. PCT/US2004/022704.
P.K. Holyoake et al; Enzyme-Linked Immunosorbent Assay for Measuring Ileal Symbiont Intracellularis-Specific Immunoglobulin G Response in Sera of Pigs;Journal of Clinical Microbiology Aug. 1994 vol. 32 No. 8 pp. 1980-1985; American Society for Microbiology.

* cited by examiner

*Primary Examiner*—Jennifer Graser
(74) *Attorney, Agent, or Firm*—Michael P. Morris; Mary-Ellen M. Devlin

(57) ABSTRACT

The present invention relates to *Lawsonia intracellularis* vaccines and methods for protecting against and diagnosing *L. intracellularis* infection. The products and processes of the invention are attainable, in part, as the result of an improved method for cultivating large scale supplies of *L. intracellularis*, including both a novel isolate of *L. intracellularis* of European origin and a method of preparing a lyophilized product containing the attenuated European isolate as vaccine product.

7 Claims, No Drawings

LAWSONIA INTRACELLULARIS OF EUROPEAN ORIGIN AND VACCINES, DIAGNOSTIC AGENTS AND METHODS OF USE THEREOF

RELATED APPLICATION

This application claims benefit to U.S. Provisional Application Ser. No. 60/490,001, filed Jul. 25, 2003, the disclosure of which is incorporated by reference in its entirety.

BACKGROUND

The present invention relates to *Lawsonia intracellularis* vaccines and methods for protecting against and diagnosing *L. intracellularis* infection. The products and processes of the invention are attainable, in part, as the result of an improved method for cultivating large scale supplies of *L. intracellularis*, including both a novel isolate of *L. intracellularis* of European origin and a method of preparing a lyophilized product containing the attenuated European isolate as vaccine product.

*L. intracellularis*, the causative agent of porcine proliferative enteropathy ("PPE"), affects virtually all animals, including: rabbits, ferrets, hamsters, fox, horses, and other animals as diverse as ostriches and emus. *L. intracellularis* is a particularly great cause of losses in swine herds in Europe as well as in the United States.

A consistent feature of PPE is the occurrence of intracytoplasmic, non-membrane bound curved bacilli within enterocytes in affected portions of intestine. The bacteria associated with PPE have been referred to as "Campylobacter-like organisms." S. McOrist et al., Vet. Pathol., Vol. 26, 260-264 (1989). Subsequently, the causative bacteria have been identified as a novel taxonomic genus and species, vernacularly referred to as *Ileal symbiont* (IS) *intracellularis*. C. Gebhart et al., Int'l. J. of Systemic Bacteriology, Vol. 43, No. 3, 533-538 (1993). More recently, these novel bacteria have been given the taxonomic name *Lawsonia* (*L.*) *intracellularis*. S. McOrist et al., Int'l. J. of Systemic Bacteriology, Vol. 45, No. 4, 820-825 (1995). These three names have been used interchangeably to refer to the same organism as further identified and described herein.

*L. intracellularis* is an obligate, intracellular bacterium which cannot be cultured by normal bacteriological methods on conventional cell-free media and has been thought to require attached epithelial cells for growth. S. McOrist et al., Infection and Immunity, Vol. 61, No. 19, 4286-4292 (1993) and G. Lawson et al., J. of Clinical Microbiology, Vol. 31, No. 5, 1136-1142 (1993) discuss cultivation of *L. intracellularis* using IEC-18 rat intestinal epithelial cell monolayers in conventional tissue culture flasks. In addition, H. Stills, Infection and Immunity, Vol. 59, No. 9, 3227-3236 (1991) discusses using Intestine 407 human embryonic intestinal cell monolayers and GPC-16 guinea pig colonic adenocarcinoma cell monolayers in conventional tissue culture flasks.

Recently, an *L. intracellularis* vaccine has been approved for use in the United States, which vaccine is based on *L. intracellularis* isolates described and claimed in U.S. Pat. Nos. 5,714,375 and 5,885,823, both of which patents are herein incorporated by reference in their entireties. The above-described vaccine is sold by Boehringer Ingelheim Vetmedica, Inc., 2621 North Belt Highway, St. Joseph, Mo. 64506-2002, under the trademark ENTERISOL® Ileitis.

SUMMARY OF THE INVENTION

One object of the invention is to provide an improved *L. intracellularis* vaccine using an isolate of European origin.

Another object of the invention is to provide an improved method for cultivation of *L. intracellularis* on a large scale and improved techniques for production of *L. intracellularis* vaccines.

To achieve these and other objects, and in accordance with the purpose of the invention as embodied and broadly described herein, the present invention provides a newly isolated *L. intracellularis* from Europe, a method of attenuating such an isolate, and the attenuated isolate thereof. Also provided herein is a vaccine comprising the attenuated isolate. Also provided herein is a method for producing a vaccine comprising the attenuated isolate in lyophilized form for reconstitution at the time of administration and the lyophilized product thereof.

In one embodiment, the newly isolated *L. intracellularis* from Europe, isolate DK 15540, is deposit isolate ATCC accession No. PTA-4927. In another embodiment, the attenuated isolate derived from isolate DK 15540, is designated isolate B3903, ATCC accession No. PTA-4926.

DETAILED DESCRIPTION

As used herein, the term "*L. intracellularis*" means the intracellular, curved gram-negative bacteria described in detail by C. Gebhart et al., Int'l. J. of Systemic Bacteriology, Vol. 43, No. 3, 533-538 (1993) and S. McOrist et al., Int'l. J. of Systemic Bacteriology, Vol. 45, No. 4, 820-825 (1995), each of which is incorporated herein by reference in their entireties, and includes but is not limited to the isolate designated DK 15540 which was deposited for patent purposes with the American Type Culture Collection ("ATCC"), 10801 University Boulevard, Manassas, Va. 20110-2209 on Jan. 9, 2003 and assigned ATCC accession number PTA-4927; the causative bacteria which can be obtained from PPE infected swine or other animals throughout the world given the knowledge in the art and the teachings herein; and variants or mutants of any of the above bacteria, whether spontaneously or artificially obtained.

As used herein, the term "attenuated isolate" means any *L. intracellularis* isolate that is prepared according to the cultivation and passaging techniques taught herein to achieve avirulence while maintaining immunogenic properties when administered to a host animal including but not limited to the attenuated isolate designated B-3903 which was deposited for patent purposes with the American Type Culture Collection ("ATCC"), 10801 University Boulevard, Manassas, Va. 20110-2209 on Jan. 9, 2003 and assigned accession number PTA-4926.

PTA-4927 and PTA-4926 were tested by the ATCC on Apr. 21, 2004, and were found viable. The date of conversion to Budapest Treaty was Oct. 16, 2007.

The attenuated isolate of the invention can be used as an immunogen in antimicrobial vaccines for animals, including birds, fish, and mammals such as cattle, swine, horses, and primates. Such vaccines can be prepared by techniques known to those skilled in the art and given the teachings contained herein. Such a vaccine would comprise an immunologically effective amount of the attenuated isolate in a pharmaceutically acceptable carrier. The vaccine could be administered in one or more doses. An immunologically effective amount is determined by means known in the art without undue experimentation, given the teachings contained herein. The amount of avirulent bacteria should be sufficient to stimulate an immune response in disease-susceptible animals while still being avirulent. This will depend upon the particular animal, bacteria, and disease involved. The recommended dose to be administered to the susceptible animal is preferably about 3.0 $TCID_{50}$ (tissue culture infective dose 50% end point)/dose to about 6.0 $TCID_{50}$/dose and more preferably about 4.0 $TCID_{50}$/dose to about 5.0 $TCID_{50}$/dose. In a preferred embodiment, the titer of the vaccine is about 4.9 $TCID_{50}$/dose as determined by Tissue Culture Infective Dose 50% endpoint dilution assay ($TCID_{50}$). The carriers are known to those skilled in the art and include stabilizers and diluents. Such a vaccine may also contain an appropriate adjuvant. The vaccines of the invention may be used in combination with other vaccines, for example, as a diluent of another vaccine. The vaccine preparations may also be desiccated, for example, by freeze drying for storage purposes or for subsequent formulation into liquid vaccines.

Accordingly, the invention also comprises a method for inducing an immune response to virulent, wild-type *L. intracellularis* bacteria in an animal host for the purpose of protecting the host from such bacteria. The method comprises administering an immunologically effective amount of the attenuated bacteria or killed bacteria of the invention to the host and, preferably, administering the vaccine of the invention to the host.

As used herein, the term "large-scale cultivation" means a level of cultivation of *L. intracellularis* greater than approximately 2.0 to 3.0 liters and includes production on a scale of 100 liters or more. "Cultivation" as used herein, means the process of promoting the growth, reproduction and/or proliferation of *L. intracellularis*.

*L. intracellularis* can be cultivated by methods known in the art, preferably, according to U.S. Pat. Nos. 5,714,375 and 5,885,823. For example, culture cells may first be inoculated with an inoculum comprising *L. intracellularis* bacteria so as to infect the cells with the bacteria. Numerous cell lines can be used in practicing the invention, including, but not limited to, IEC-18 (ATCC 1589)-rat intestinal epithelial cells, HEp-2 (ATCC 23)-human epidermoid carcinoma cells, McCoys (ATCC 1696)-mouse (non-specified) cells, BGMK (Biowhittaker #71-176)-buffalo green monkey kidney cells, and swine intestinal epithelium cells. The preferred culture cells are HEp-2, McCoys or IEC-18 cells.

If culture cells are used, prior to being inoculated, the cells may be in the form of a monolayer. To form a monolayer, the cells may be seeded into conventional flasks. Each flask is generally seeded with between about $1 \times 10^5$ cells to about $10 \times 10^5$ cells per 25, 75, 150, 850 $cm^2$ flask or roller bottle mixed with growth media. The growth media may be any media for cell cultivation which includes a nitrogen source, necessary growth factors for the chosen culture cells, and a carbon source, such as glucose or lactose. The preferred media is DMEM fortified with Ham's F 12 with 1-5% fetal bovine serum, although other commercially available media may be used with good results.

Successful cultivation of *L. intracellularis* is enhanced by maintaining the culture cells in a constant state of growth. Therefore, the culture cell monolayer should be at about 20 percent to about 50 percent confluency at the time of inoculation. Preferably, the cells should be at about 30 percent to about 40 percent confluency at the time of inoculation, most preferably at about 30 percent confluency.

Alternatively, the cells, prior to being inoculated, may be grown in suspension, as described infra. Preferably, the cells are first grown to 100% confluency in the form of a monolayer in an adherent type system, e.g., a roller bottle system, and then transferred to 3-3000 liters and grown in suspension. Alternatively, the cells can be grown in suspension to the desired cell density, e.g. $2 \times 10^5$ cells/ml, within the 3-3000 liter vessel (bioreactor, Fermentor, spinner flask, etc.) using parameters suitable for growth within this system prior to inoculation.

The inoculum may be a pure culture of *L. intracellularis* obtained from infected swine or other animals. Preferably the inoculum may be a pure culture of *L. intracellularis* obtained from ATCC accession No. PTA-4927.

The inoculum can be an intestinal homogenate prepared by scraping the mucosa off of the ileum of a swine or other animal infected with PPE. When preparing an intestinal homogenate, ileal sections selected for culture should show severe lesions with gross thickening of the gut. Due to the fragile nature of the bacteria, samples should preferably be stored at $-70°$ C. as quickly as possible after necropsy. An antibiotic to which *L. intracellularis* is resistant such as Vancomycin, Amphotericin B or members of the aminoglycoside group of antibiotics, including Gentamicin and Neomycin, to name a few, is preferably added to the inoculum to suppress contaminating bacteria while permitting *L. intracellularis* growth. Whether the inoculum is a pure culture or an intestinal homogenate, inoculation of the culture cells can be performed by various techniques known in the art, given the teachings herein.

The bacteria and/or inoculated culture cells are then incubated under a reduced dissolved $O_2$ concentration. At dissolved oxygen concentrations greater than 10% *L. intracellularis* growth is less than optimal with cessation of growth eventually occurring at oxygen concentrations outside this range. Preferably, the bacteria and/or inoculated culture cells are incubated in a dissolved oxygen concentration in the range of about 0% to about 10%. More preferably, the bacteria and/or cells are incubated in an oxygen concentration in the range of about 0% to about 8%, with an oxygen concentration of about 0% to about 3.0% being most preferred.

The proper concentration of carbon dioxide is also important to the proper growth of *L. intracellularis*. At carbon dioxide concentrations greater than 0% and less than 4%, non-optimum growth occurs with cessation of growth eventually occurring at carbon dioxide concentrations outside this range. Preferably, the carbon dioxide concentration is in the range from about 6% to about 10%, with a carbon dioxide concentration of about 8.8% being most preferred.

In addition, the cells are preferably incubated at a hydrogen concentration in the range from about 4% to about 10%. Most preferably, the cells are incubated in about 0 to about 8.0% $O_2$, about 8.8% $CO_2$, and about 4% $H_2$. Nitrogen is used as a "balance" in the gas mixture containing nitrogen (96%) and hydrogen (4%) or nitrogen (80%), carbon dioxide (10%) and hydrogen (10%) for growth of this organism. Cells are preferably incubated at a nitrogen concentration in the range from about 80% to 96%. Therefore, cells are most preferably incubated in about 0 to about 8.0% $O_2$, about 8.8% $CO_2$, about 4% $H_2$ and about 96% $N_2$.

Inoculated cells may be incubated in a dual gas incubator or other gas chambers which contain the proper hydrogen, oxygen and carbon dioxide concentrations and which allow the cells to be suspended during incubation. The chamber should comprise a means for maintaining the inoculated cells in suspension, and a gas monitor and supply source to supply and maintain the proper gas concentrations. The incubation temperature should be in the range of from 30° C. to about 45° C. and is more preferably in the range of from about 36° C. to about 38° C. Most preferably, the temperature is about 37° C. The necessary equipment for cultivation and attenuation is readily available to those of ordinary skill in the art given the teachings herein. One example of equipment suitable for carrying out the present invention is a dual gas incubator, e.g., model 480 (Lab-Line, Melrose Park, Ill.) in conjunction with spinner flasks to maintain the cells in suspension. The presently preferred equipment comprises a fermentor, bioreactor, stir plate or rotary shaker containing at least about 2 liters media and capable of maintaining the culture cells in suspension via sparging gas of the appropriate concentration, or other means of mechanical agitation, and continuously monitoring dissolved $O_2$ levels in the media. New Brunswick, Braun and other companies make suitable fermentors and bioreactors for this purpose.

By maintaining the inoculated cells in a suspended state during incubation, maximum growth of the cells, and hence L. intracellularis, is achieved by increasing each individual cell's exposure to growth media and the proper mixture of hydrogen, oxygen and carbon dioxide. The culture cells can be agitated and maintained in suspension by a variety of methods known in the art including, for example, culture flasks, roller bottles, membrane cultures, biobags, WAVE® bioreactor systems, fermentors and spinner flasks. The cells may be kept in suspension during incubation by incubating the cells in a spinner flask inside a dual gas incubator or similar apparatus. The term "spinner flask", as used herein, means a flask or other container which employs a paddle, propeller or other means to agitate the culture and keep the cells contained therein in suspension.

In a preferred embodiment, the inoculated cells are incubated until the cells reach confluency and then the cells are placed in a spinner flask containing growth media and incubated in a dual gas incubator while spinning the flask. Preferably, the inoculated cells are scraped or trypsinized and passaged into the spinner flask. This can be achieved by a variety of methods known in the art such as using a cell scraper to detach the cells. Once the cells are introduced into the spinner flask, the paddle of the spinner flask is typically rotated in the range of from about 5 to about 500 rpm on a magnetic stir plate in order to maintain the infected cells in suspension.

A portion of the cultivated L. intracellularis is then passaged to fresh culture to increase the production of L. intracellularis bacteria. The term "passaging" or variations thereof herein means the process of transferring a portion of the cultivated L. intracellularis to fresh culture cells in order to infect the fresh cells with the bacterium. The term "fresh", as used herein, means cells which have not yet been infected by L. intracellularis. Preferably such cells are on the average no more than approximately one day old.

The passage of L. intracellularis in suspension cultures may be accomplished by removing a portion of the original culture and adding it to a new flask containing fresh culture cells. If the original culture has a high number of bacteria/ml, for example, greater than about $10^4$ bacteria/ml, it is preferable to add between about 1 to 10% (volume to volume) of culture from the infected flask to a new flask containing fresh cells. This is preferably done when 50-100% of the cells are infected. If fewer than 50% of the cells are infected, passaging is preferably accomplished by splitting the culture 1:2 into a new flask and scaling-up the volume by adding fresh tissue culture cells and media. In either case, cell lysis and other steps are not required, in direct contrast to the passage of monolayer cultures, as in the prior art.

After sufficient growth of the culture cells and subsequent infection by L. intracellularis, as determined by indirect fluorescent antibody (IFA) staining, $TCID_{50}$ or another comparable method, at least a portion of the cultivated L. intracellularis bacteria is then harvested. Harvesting is typically performed at cell infectivity of about 60% or higher; however, one skilled in the art knows that harvesting could be performed at a cell infectivity of less than 60%. The harvesting step may be performed by separating the bacteria from the suspension by various techniques known to those of ordinary skill in the art, given the teachings herein. Preferably, the L. intracellularis bacteria is harvested by centrifuging the contents of all or a portion of the suspension to pellet the culture cells, resuspending the resulting cell pellets, and lysing the infected cells. Typically, at least a portion of the contents is centrifuged at about 3000×g for about 20 minutes in order to pellet the cells and bacteria. The pellet may then be resuspended in, for example, a sucrose-phosphate-glutamate (SPG) solution and passed approximately 20 times through a 25 gauge needle in order to lyse the cells. If further purification is desired, the samples can be centrifuged at about 145×g for about five minutes to remove cellular nuclei and debris. The supernatant may then be centrifuged at about 3000×g for about twenty minutes and the resulting pellet resuspended in an appropriate diluent, such as SPG with fetal bovine serum (to prepare harvested bacteria suitable for lyophilization, freezing, or use as an inoculant) or growth media (to prepare harvested bacteria more suitable for passaging to fresh cells).

As previously mentioned, effective growth of L. intracellularis for large-scale production is enhanced by keeping the tissue cells actively growing. With monolayers, when cultures become confluent, the rate of cell division decreases substantially. Attempts to grow L. intracellularis on monolayer tissue cultures have had limited success and scale-up has not been possible. However, using suspension cultures greatly facilitates keeping the cells actively growing and permits continuous culture expansion and scale-up. Using a fermentor and between about 0 to 3% dissolved $O_2$ as explained above, enables growth of up to and greater than $10^8$ bacteria/ml.

When using IEC-18 cells, it is preferable to add gelatin, agarose, collagen, acrylamide or silica beads, such as Cultisphere-G porous microcarriers (HyClone Laboratories, Logan Utah), along with the growth media. However, HEp-2 cells and others do not require microcarriers according to the methods used herein.

For culture maintenance purposes, with HEp-2 cultures, preferably 25% to 50% of the culture is removed and replaced with fresh media at weekly intervals. For cell cultures with microcarriers or beads, preferably 25% to 50% of the culture is removed and replaced with fresh media 1-2 times weekly. For scale-up purposes, an additional 25% to 50% of media, or media with microcarriers, may be added to the culture.

Depending upon the rate at which the culture cells become infected, passage to fresh cells generally occurs between about every 2 to about 7 days. Assuming that the culture cells become at least 70% infected within 2 to 7 days, preferably passage occurs between about every 5 to 7 days.

The present invention also provides vaccines and methods for producing vaccines against a novel isolate of L. intracellularis of European origin. Preferably, after maintaining the infected cells in suspension for an extended time (for example, 6-8 months), at least a portion of the cultivated L. intracellularis bacteria are harvested and monitored for potential attenuation. Such monitoring is preferably accomplished by host animal or animal model challenges to select for an attenuated isolate. Such attenuated isolates are used in vaccines according to the methods taught herein.

The present invention allows rapid culture expansion, an increase in yields of 100-1000 fold, and reduced cost for production of L. intracellularis of European origin. As a result, the abundant supply of L. intracellularis bacteria produced is readily attenuated for vaccine production purposes. The method of growing L. intracellularis in suspension greatly increases the ease, speed, and number of bacterium available for this purpose. The more cells and cell divisions which occur, the greater the level of mutations occurring which are advantageous in vaccine development. Thus, growth in suspensions increases the expression of important immunogens controlled by environmentally regulated genes and their expression products.

The resulting attenuated isolates can be cultivated in tissue culture monolayers but are preferably cultivated in suspension cultures. Other means of attenuation can include chemical attenuation by the use of, for example, N-methyl nitrosoguanidine and others known in the art. Whether by multiple passage or chemical means, an attenuated L. intracellularis is produced and selected for vaccine preparation. In a preferred embodiment, the resulting attenuated isolate is ATCC accession No. PTA-4926.

The vaccine antigen can be harvested by centrifugation or microfiltration as described above. The antigen is then standardized at a defined level based on the optimum host animal immune response, determined by a dose titration in the host animal species. The bacteria may be inactivated by methods known in the art, e.g., by using 0.3% formalin or other inactivating agents to prepare a killed vaccine. The antigen is then incorporated into a suitable adjuvant, such as aluminum hydroxide or mineral oil to enhance the immune response. The antigen is then used to vaccinate the host via intramuscular or subcutaneous infection, in the case of swine at about 3-4 weeks of age, with a booster dose if necessary.

Preferably, the bacteria is serially passaged to induce and select for an attenuated, avirulent live culture. The culture is tested in the host animal for signs of attenuation. The culture is harvested as described earlier and lyophilized. Swine, for example, are orally vaccinated with $1\times10^4$ to $1\times10^6$ bacteria. About twenty-eight days after vaccination, the swine are orally inoculated with about $1\times10^7$ organisms from a less passaged (less than 30 passages in vitro past the original isolation from the intestinal homogenate) virulent culture of L. intracellularis. Infected animals are necropsied 21 days after challenge and the small intestines observed for gross lesions as well as microscopic lesions. PCR, indirect fluorescent antibody (IFA) or immunohistochemistry (IHC) should also be performed.

About eighty percent of the control animals will show gross or microscopic lesions and test positive for the presence of L. intracellularis in the mucosal cells of the intestines using either PCR, IFA or IHC testing methods. Vaccinated animals will have normal mucosal surfaces as determined by histological observations and will be negative by PCR testing 3 to 4 weeks post inoculation.

Generally, an attenuated immunogenic L. intracellularis isolate is produced after continuous culture for about 150 days to about 250 days, during which time the culture is passaged about 50-100 times. However, one skilled in the art knows that other attenuated cultures may be produced by varying these figures.

The vaccine product of the invention can be lyophilized. After harvesting, the isolate can be concentrated by various methods known in the art and can be mixed with a stabilizer, e.g. sucrose gelatin stabilizer. The vaccine product can then be subjected to freezing and drying (lyophilization). Generally, the freezing step comprises ramping to about −45° C.±3° C. and holding for about 150 minutes to about 480 minutes. The drying step can comprise primary and secondary drying steps. For example, the primary drying step can comprise: (a) ramping to between about −30° C. to about −5° C. and holding for between about 120 minutes to about 1000 minutes, and, optionally (b) ramping to between about −5° C. to about 5° C. and holding for between about 150 minutes to about 2000 minutes. The secondary step generally comprises ramping to about 27° C.±5° C. and holding for between about 330 minutes to about 1120 minutes. One skilled in the art knows that these ranges can be adjusted depending on conditions, e.g., starting volume.

A vaccine is then prepared comprising an immunologically effective amount of the attenuated L. intracellularis in a pharmaceutically acceptable carrier. In a preferred embodiment, a vaccine comprises ATCC accession No. PTA-4926 in a pharmaceutically acceptable carrier. The combined immunogen and carrier may be an aqueous solution, emulsion or suspension. An immunologically effective amount is determinable by means known in the art without undue experimentation given the teachings contained herein. In general, the quantity of immunogen will be between 5 and 5000 micrograms, and between $10^{2.0}$ and $10^{9.0}$ TCID$_{50}$, preferably between $10^{3.0}$ and $10^{6.0}$ TCID$_{50}$, more preferably between $10^{4.0}$ and $10^{5.0}$ TCID$_{50}$, when purified bacteria are used.

The present invention also encompasses combination vaccines comprising the attenuated L. intracellularis isolate designated ATCC accession No. PTA-4926 and antigenic material from at least one other pathogen, including but not limited to: Salmonella spp. (e.g., Salmonella choleraesuis, Salmonella typhimurium), Erysipelothrix spp. (e.g., Erysipelothrix rhusiopathiae), Haemophilus spp. (e.g., Haemophilus parasuis), Mycoplasma spp. (e.g., Mycoplasma hyopneumonia), Leptospira spp., Clostridium spp. (e.g., Clostridium perfingens, Clostridium difficile), Streptococcus spp. (e.g., Streptococcus suis), Brachyspira spp. (e.g., Brachyspira hyodysenteriae), Bordetella (e.g., Bordetella bronchiseptica), Pasteurella spp. (e.g., Pasteurella multocida), circovirus (e.g., porcine circovirus type 2), porcine reproductive and respiratory syndrome (PRRS) virus, swine influenza virus (SIV), coronovirus (e.g., transmissible gastro-enteritis (TGE) virus, porcine respiratory corona virus), parvovirus, or Escherichia coli; and a pharmaceutically acceptable carrier.

In one embodiment, the combination vaccine comprises the attenuated L. intracellularis isolate designated ATCC accession No. PTA-4926 and antigenic material from Salmonella choleraesuis, Erysipelothrix spp. Clostridium spp, Brachyspira spp., transmissible gastro-enteritis (TGE) virus, and Escherichia coli; and a pharmaceutically acceptable carrier. Antigenic material from Clostridium spp. can include, but is not limited to, Clostridium perfingens and Clostridium difficil. Antigenic material from Erysipelothrix spp. can include, but is not limited to, Erysipelothrix rhusiopathiae.

In another embodiment, the combination vaccine comprises the attenuated L. intracellularis isolate designated ATCC accession No. PTA-4926 and antigenic material from Salmonella choleraesuis and Erysipelothrix spp.; and a pharmaceutically acceptable carrier. In another embodiment, the combination vaccine comprises the attenuated L. intracellularis isolate designated ATCC accession No. PTA-4926 and antigenic material from *Salmonella choleraesuis* and *Erysipelothrix rhusiopathiae*; and a pharmaceutically acceptable carrier.

In another embodiment, the combination vaccine comprises the attenuated *L. intracellularis* isolate designated ATCC accession No. PTA-4926 and antigenic material from at least one other pathogen, including but not limited to: *Clostridium* spp. e.g., *Clostridium tetani*), equine influenza virus (EIV) (e.g., EIV-1, EIV-2), equine herpes virus (EHV) (e.g., EHV-1, EHV-2, EHV-3, EHV-4, EHV-5, EHV-6, EHV-7,), alphavirus (e.g., eastern encephalitis virus, western encephalitis virus, Venezuelan encephalitis virus), or West Nile virus.; and a pharmaceutically acceptable carrier.

The vaccines according to the invention are generally administered to susceptible animals, preferably swine, in one or more doses. The live or killed vaccine may be administered 1 or 2 times at 2 week intervals. For the attenuated, live vaccines, one dose is preferred. The preferred routes of administration of attenuated live isolates are intramuscular, oral or intranasal, but intramuscular and subcutaneous injection routes are most preferred for the killed vaccine.

Effective diagnosis of PPE has also been hindered by the time required to culture the causative bacteria. As a result of the present invention, development of diagnostic tools promoting rapid and accurate assays for the presence of *L. intracellularis* in biological samples taken from swine and other animals susceptible to PPE is now possible.

The *L. intracellularis* bacteria of European origin of the instant invention, or components derived from such bacteria, can be used as an antigen in an ELISA or other immunoassay, such as an immunofluorescent antibody test ("IFA"), to detect antibodies to *L. intracellularis* in the serum and other body fluids of animals suspected of being infected with the bacteria. The presently preferred immunoassay is an IFA as described in the example below. Alternatively, the bacteria of the instant invention can be used in a Western Blot assay.

The preferred ELISA protocol according to the invention is as follows:
1. Add 0.1 ml/well antigen diluted in coating buffer. Incubate for 18 hours at 4° C.
2. Wash 3 times with PBS.
3. Add 0.25 ml of blocking buffer to each well of plate. Incubate 1 to 2 hours at 37° C.
4. Wash 3 times with wash buffer.
5. Dilute serum in blocking buffer and add 0.1 ml to the first wells of plate. Make serial 1:2 dilutions across the plate. Incubate for 1 hour at 37.
6. Wash 3 to 5 times with wash buffer.
7. Dilute conjugate in blocking buffer and add 0.1 ml to wells of plate and incubate for 1 hour at 37° C.
8. Wash 3 to 5 times with wash buffer.
9. Add substrate.
10. Measure absorbance of light with a spectrophotometer.
11. Wells in which antigen was not added are used as blanks.
12. Positive and negative control swine serum should also be used with each test.

The preferred Western Blot protocol is as follows:
1. Run antigen on 12% SDS-PAGE and transfer to nitrocellulose membrane.
2. Place membrane in blocking buffer for 2 hours.
3. Remove blocking buffer and rinse with PBS for 1 minute.
4. Dilute serum in blocking buffer and add to membrane. Incubate for 2 hours at room temperature.
5. Wash 3 times with wash buffer (5 minutes for each wash).
6. Dilute conjugate in blocking buffer and add to membrane. Incubate for 1 hour at room temperature.
7. Wash 3 times with wash buffer.
8. Add substrate for 10 minutes or until strong banding occurs.
9. Rinse with PBS.
10. Air dry and store in the dark.

The *L. intracellularis* bacteria of European origin of the instant invention, or components derived from such bacteria, can also be used to prepare antiserum or antibodies for diagnostic, prophylactic, or therapeutic use. The *L. intracellularis* bacteria of European origin of the instant invention, or components derived from such bacteria, can be administered to a non-human animal in an amount effective to elicit an immune response and the antiserum or plasma containing antibodies to the *L. intracellularis* bacteria, or components derived from such bacteria, can be collected according to methods known in the art and described herein.

The present invention is further described in the following examples which are provided for illustrative purposes only and are not to be construed as limiting. Indeed, other variants of the invention will be readily apparent to one of ordinary skill in the art.

All publications and patents cited herein are incorporated by reference in their entireties.

EXAMPLE 1

Production of *L. Intracellularis* Vaccine

Isolation and Attenuation of *L. intracellularis* from the Intestines of European Pigs with Porcine Proliferative Enteropathy (PPE):

*L. intracellularis* virulent isolate DK 15540 (DK 15540, DK-15540 and 15540 are used interchangeably herein) was isolated by the University of Minnesota from an ileal homogenate of a Danish pig infected with acute porcine hemorrhagic enteropathy. This isolate has been deposited under the Budapest Treaty with the American Type Culture Collection, 10801 University Boulevard, Manassas, Va. 20110-2209 and assigned accession number PTA-4927. The isolation process included scraping the mucosa from the ileum, homogenizing, trypsinizing for 30 minutes, and passing through a tissue grinder. The ileal homogenate was then passed through a series of filters consisting of 5.0, 1.0, and 0.65 µm. The homogenate was diluted in sucrose phosphate glutamate buffer with 10% fetal bovine serum (FBS). Aliquots (6×1 ml) of homogenate were made and stored at less than −70° C. The homogenate was used as inoculum to infect T-75 $cm^2$ flasks of McCoy cells. Cultures were monitored daily for McCoy cell infection by scraping McCoy cell monolayers, lysing cells by potassium chloride treatment, and placing the concentrated cell pellet on microscope slides stained by IFA using monoclonal antibodies specific for *L. intracellularis*. After eleven passages on anchorage dependent cell cultures, inoculum from passage eleven was transferred into a 250 ml spinner flask containing McCoy cells and grown in suspension until harvest. The Danish isolate of *L. intracellularis* (ATCC accession No. PTA-4927) was attenuated by continuous in vitro passage in McCoy cells for 80 weeks and tested for identity by monoclonal antibodies. The attenuated isolate was designated B3903 (B3903, B 3903 and B-3903 are used interchangeably herein). Isolate B3903 was deposited under the Budapest Treaty with the American Type Culture Collection, 10801 University Boulevard, Manassas, Va. 20110-2209 and assigned ATCC accession No. PTA-4926.

Cultures:

Identification

Characteristic growth requirements, PCR reactions, and monoclonal antibody reactions were used to identify *L. intracellularis* Master and Working Seed materials.

Purity

Purity of Master Seed and Working Seed of *L. intracellularis* was determined by examining cultures with monoclonal antibody stains, conventional extraneous agents tests for bacteria and viruses and by sterility mycoplasma tests.

Virulence

Master Seeds of *L. intracellularis* were not virulent as demonstrated by the lack of ability of the Master Seed and Back passage inoculum to produce clinical signs and gross lesions that are observed in susceptible swine following exposure of virulent *L. intracellularis*, as further illustrated in Example 2, infra.

Range of Subcultures

Final harvested material from production of *L. intracellularis* did not exceed eleven passages from the Master Seed.

Medium Composition

EU McCoy Master Cell Stock (MCS) were grown and maintained in Dulbecco's Modified Eagle Medium with Ham's Fortified F12 (DMEM/F12) and 1-10% (v/v) newborn bovine serum (NBS) or fetal bovine serum (FBS) (cell growth and maintenance media).

Master and Working Seed were stored in DMEM/F12 with 1-10% (v/v) NBS or FBS and 5-15% (v/v) glycerol (master and working seed storage media).

The final harvest product was stored in sucrose gelatin stabilizer (SGS) (final product storage media).

Propagation

Master and Working Seed cultures of *L. intracellularis* were propagated in EU McCoy MCS using cell growth and maintenance media as described supra and stored at less than or about −35° C.

Source of Tissue

*L. intracellularis* seed and production organisms were grown in McCoy Master Cell Stock (ATCC accession number CRL 1696, batch number F-10422). The mast cell stock was identified as 3894MMCSS at passage X. The master cell stock was passaged an additional six times and identified as EU McCoy MCS X+0. EU McCoy MCS passage X+0 was stored at −70° C.±5° C. or colder. Production vaccine was made in EU McCoy MCS cell line subcultures through the $40^{th}$ passage.

Culture Containers

EU McCoy MCS were propagated in tissue culture flasks with 25-150 cm$^2$ surface area, Costar cell cubes, in roller bottles with 850 cm$^2$ to 2, 2250 cm$^2$, in spinner flasks up to 40 L capacity, and in bioreactors having 3 L to 500 L capacity.

Seed cultures of *L. intracellularis* were grown in 250-40,000 ml spinner flasks, 850 cm$^2$ to 2,250 cm$^2$ roller bottles, tissue culture flasks with 25-150 cm$^2$ surface area, or in bioreactors having 3 L to 500 L capacity.

Production cultures of *L. intracellularis* were grown in 6 L to 40 L spinner flasks or in bioreactors having 3 L to 500 L capacity.

Methods of Preparing Suspensions for Seeding or Inoculation

Seeding Cultures

Frozen or fresh *L. intracellularis* Master or expanded Working Seeds were thawed at room temperature (25° C.±3° C.) or at 37° C.±2° C. Bioreactors, spinner flasks or bottles previously seeded with McCoy cells at a cell density of 50,000 to 500,000 cells/ml were infected with *L. intracellularis* at a concentration of 1 to 10% (v/v) or MOI of 0.08 to 1.0. The infected culture was incubated under reduced oxygen concentrations by overlaying with a gas mixture composed of 86% $N_2$, 4% $H_2$ and 10% $CO_2$. The culture was incubated for 3 to 10 days at 37° C.±2° C., pH 6.7 to 7.3, and with continuous agitation (10 to 100 rpm) to maintain adequate mixing for the cells to remain in suspension.

Production Cultures

Frozen or fresh *L. intracellularis* Master or expanded Working Seeds were thawed at room temperature (25° C.±3° C.) or at 37° C.±2° C. Bioreactors or spinner flasks 3 L to 500 L capacity) previously seed (0 to 7 days) with McCoy cells at a cell density of 50,000 to 500,000 cells/ml were infected with *L. intracellularis* at a concentration of 1 to 10% (v/v) or MOI of 0.08 to 1.0. The infected culture was incubated under reduced oxygen concentrations by overlaying or sparging with a gas mixture composed of 96% $N_2$, 4% $H_2$.

The culture was incubated for 3 to 8 days at 37° C.±2° C., pH 6.7 to 7.3, and with continuous agitation (10 to 100 rpm) to maintain adequate mixing for the cells to remain in suspension.

Inoculation Techniques for Seed and Production Cultures

Seed Cultures

Up to 10% (v/v) of Master or Working Seed are inoculated (MOI=0.08 to 1.0) into bioreactors, spinner flasks or bottles seed with McCoy cells at 0-7 days in growth medium.

Production Cultures

Up to 10% (v/v) of Production Seed was inoculated (MOI=0.08 to 1.0) into an appropriate volume of growth medium seeded with McCoy cells at 0 to 7 days with the appropriate McCoy cell density in 3 L to 500 L capacity vessels.

Incubation of Microorganisms

The cultures were incubated at 37° C.±2° C. for 3 to 10 days in a reduced oxygen atmosphere with agitation to maintain the suspension. Additional medium and/or McCoy cells can be added to continue the growth process.

Cultures were observed macroscopically during the incubation period for evidence of abnormal growth or signs of contamination.

Harvest:

Handling and Preparation of Cultures

Cultures were examined for signs of adequate bacterial growth by indirect fluorescent antibody (IFA) staining. Cultures that were ready for harvest exemplified 60 to 100% cell infectivity. Percent infectivity was determined by observation of at least three fields, each field containing enough McCoy cells to fill at least 80% of the area. To be considered infected, approximately 50% of the cell is filled with bacteria.

Potency of the harvest culture is tested by titration of the sample on McCoy cells which are fixed and stained using specific monoclonal antibody (anti-*L. intracellularis* monoclonal antibody VPM 53 Lot 31599 or equivalent; antimouse IgG-fluorescein conjugate (FITC) (ICN No. 55499) after 6 days of incubation at 37° C.±2° C.

Cultures were examined visually for any obvious signs of contamination. Harvest occurred 3 to 10 days post inoculation.

Harvesting Techniques and Specifications

Cell and fluid contents in the production culture bioreactor, spinner flasks and bottle were partially or fully collected in a sterile receiving vessel. Each production culture bioreactor, spinner flask and bottle was harvested individually or the contents of several vessels were pooled with the addition of SGS and stored at 1° C. to 7° C. or colder. Harvested production culture was sampled for potency by $TCID_{50}$ and identification by IFA staining.

Production cultures exhibited at least 4.9 $TCID_{50}$/ml by IFA staining and were free of any evidence of contamination upon microscopic observation.

Preparation of Vaccine Product:

Concentration Methods

The vaccine product can be concentrated by various methods, e.g., by allowing the culture to settle with subsequent decanting of the supernatant, by membrane filtration (0.22 μm or smaller), perfusion, or by centrifugation.

Sucrose Gelatin Stabilizer (SGS)

Hydrolyzed gelatin solution is prepared by mixing gelatin with deionized water or water for injection at approximately 25% final total volume of SGS batch size and hydrolyzing in an autoclave for 120 minutes at 121° C.

The hydrolyzed gelatin solution (40.0 g/L) was then mixed with deionized water or water for injection at approximately 75% final total volume of SGS batch size. Potassium hydroxide (AR) (0.548 g/L), L-glutamic acid (1.440 g/L), dipotassium phosphate (AR) (2.508 g/L), potassium dihydrogen phosphate (AR) (1.030 g/L), and sucrose (AR) (150.00 g/L) were added and the solution was thoroughly mixed. The pH of the stabilizer was then adjusted to 6.8 to 7.0 with hydrochloric acid or sodium hydroxide solutions. Deionized water or water for injection was added to 100% of desired final volume of the SGS. The complete stabilizer was thoroughly mixed, and the entire solution was sterilized by filtration through a 0.1 micron filter.

Example of Assembly of Units to Make a Serial is shown in Table 1:

TABLE 1

| L. intracellularis | 200,000-300,000 ml |
|---|---|
| sucrose gelatin stabilizer (SGS) | 100,000 ml (25% v/v) |
| DMEM/F12 (May be added to standardize the product) | 0-150,000 ml |
| TOTAL VOLUME | 400,000 ml |

Volume of an average serial was 50 L to 500 L.

Lyophilization

The vaccine product was lyophilized according to the procedure outlined in Table 2 for a 10 dose cycle (6.0 ml fill) or Table 3 for a 50/100 dose cycle (10.0 ml fill).

TABLE 2

| STEPS | ° C. | Rate (minutes) | Hold (minutes) | Pressure (mT) |
|---|---|---|---|---|
| PRE-COOL* | 5° | Na | Na | Atm |
| FREEZE | −47° ± 3° | As fast as possible | 150 | Atm |
| 1° DRYING, 1st | −15° ± 2° | 120 | 120 | 100-150 |
| 1° DRYING, 2nd | 0° ± 2° | 120 | 180 | 100-150 |
| 2° DRYING, 1st | 32° ± 2° | 240 | 180 | 60-80 |
| 2° DRYING, 2nd | 26° ± 2° | 240 | As fast as possible | 60-80 |

Total Time: 1352 minutes (22.5 hrs)
*Shelves are pre-cooled to 5° ± 2° C. during the loading of the lyophilizer.

TABLE 3

| STEPS | ° C. | Rate (minutes) | Hold (minutes) | Pressure (mT) |
|---|---|---|---|---|
| PRE-COOL* | 5° | N/A | N/A | Atm |
| FREEZE | −48° ± 3° | 60 | 90 | Atm |
| 1° DRYING | −15° ± 2° | 60 | 1500 | 100-150 |
| 2° DRYING | 26° ± 2° | 60 | 600 | 60-80 |

Total Time: 2370 minutes (39.5 hrs)
*Shelves are pre-cooled to 5° ± 2° C. during the loading of the lyophilizer.

EXAMPLE 2

Safety of L. Intracellularis Vaccine

Purpose:

The objectives of this study were two-fold. The first objective of this study was to observe and compare the incidence of disease caused by three different low passage isolates (two of U.S. origin and one of European origin) of L. intracellularis in pigs at 6½ weeks of age. The second objective was to observe the safety of two high passage isolates (both of European origin) of L. intracellularis in pigs at 6½ weeks of age.

Materials and Methods:

Test Substances
1. L. intracellularis low passage U.S. isolate N343
2. L. intracellularis low passage U.S. isolate N101494.
3. L. intracellularis low passage EU isolate DK 15540 p20
4. L. intracellularis high passage EU isolate DK 15540 p60
5. L. intracellularis high passage EU isolate DK 15540 p80 (Master Seed designation B3903).

Formulation of Test Substances

Low passage isolates were grown continuously for 10-20 weeks after isolation in McCoy cell suspension. High passage isolates were grown continuously for 60-80 weeks after isolation in McCoy cell suspension. All cultures were harvested via centrifugation at 10,000 RPM for 15 minutes. The McCoy cell culture pellets containing Lawsonia were resuspended in Sucrose-Phosphate-Glutamine (SPG) solution with 10% FBS.

Storage of Test Substances

Harvested cultures were stored at −70° C. until the day of challenge. Challenge cultures of the same isolate but from various harvest dates were thawed and combined into plastic vaccine bottles, labeled, and stored at 4° C. or on ice until the time of challenge.

Assay of Test Substances $TCID_{50}$ was performed on all pooled challenge isolates at the time of challenge (day 0). The average titers (n=3) ($TCID_{50}$/ml) were as follows in Table 4:

TABLE 4

| Test Substance | Average Titer ($TCID_{50}$/ml) |
| --- | --- |
| L. intracellularis N343 | 6.4 |
| L. intracellularis N101494 | 6.1 |
| L. intracellularis DK 15540 p20 | 6.2 |
| L. intracellularis DK 15540 p60 | 6.87 |
| L. intracellularis DK 15540 p80 | 7.4 |

Study Design

The study consisted of five experimental groups and one control group. On day 0 of the study, Group 1 (10 pigs, 6½ weeks of age) received one 10 ml or equivalent intragastric (IG) dose of L. intracellularis low passage U.S. isolate N343. Group 2 (10 pigs, 6½ weeks of age) received one 10 ml or equivalent IG dose of L. intracellularis low passage U.S. isolate N101494. Group 3 (10 pigs, 6½ weeks of age) received one 10 ml or equivalent IG dose of L. intracellularis low passage EU isolate DK15540 p20. Group 4 (10 pigs, 6½ weeks of age) received one 10 ml or equivalent IG dose of L. intracellularis high passage EU isolate DK15540 60 week. Group 5 (20 pigs, 6 weeks of age) received one 10 ml or equivalent dose of L. intracellularis high passage EU isolate DK 15540 p80. Group 6 (10 pigs, 6½ weeks of age) designated as "Strict Controls" did not receive a treatment.

Daily health observations were made from initiation of study to the day of challenge of appropriate test animals. Clinical health (behavior, appetite, body condition, hair coat, and stool consistency on a scale of 1 to 4 were scored daily from day of challenge (day 0) to termination of study (day 21). Average daily weight gains (ADWG) were calculated from day of challenge (day 0) to termination of study (day 21). Fecal shedding of L. intracellularis was evaluated on days 0, 7, 14, and 21. The one animal that died (from Group 1) throughout the study was examined for gross and microscopic lesions. Death was determined to be due to lesions associated with PPE confirmed by histology and PCR analysis; the animal was not replaced. Qualitative analysis of Lawsonia content in feces was evaluated by PCR along with histological evaluation for L. intracellularis on the ileum and colon. Serum was collected on days 0, 7, 14, and 21 of the study.

Results:

Summary of Study Results

General Observations

Daily health observations were made until challenge. The clinical condition of the animals was evaluated daily following challenge for the duration of the study. Observations included: behavior, appetite, body condition, hair coat, and stool consistency. The clinical conditions of these animals were evaluated based on a numerical point system, which reflects the severity of illness. Scores ranged from 1 to 4 for each parameter. A score of 1 was given to an animal with a normal, healthy appearance, a score of 3 for an animal demonstrating severe clinical signs, and a score of 4 for an animal that has deceased. The average daily score for the strict controls, DK15540 p60, and DK15540 p80 was 5.0. The average daily scores for low passage material was N343 (5.23), N101494 (5.15), and DK15540 p20 (5.01). Statistical analysis on these results indicated no differences among treatment and control groups using Kruskal-Wallis Rank Sum Test.

Average Daily Weight Gains (ADWG)

Average daily weight gains were calculated from the time of challenge (day 0) to the termination of the study (day 21). The average weight gain per day for the strict control group was 0.9 pounds. The average weight gain for the low passage treatment groups was only 0.6 (N343), 0.8 (N101494), and 0.86 (DK15540 p20) pounds/day. The high passage treatment groups revealed the same or increased average weight gain per day compared to the strict control group that didn't receive challenge with 0.9 pounds/day (DK15540 p60) and 1.05 pounds/day (DK15540 p80) respectively. The mean difference in average daily weight gains was significantly lower in the N343 treatment group compared to higher passage treatment groups (DK15540 p60 and p80) and strict control group at day 21 of the study. (Pearson Chi-square p<0.05).

Seroconversion

Seroconversion to Lawsonia exposure in pigs was measured by testing for the presence of anti-Lawsonia antibodies using an IFAT assay. On day 0, only the N343 treatment group observed detectable seroconversion in 2/10 pigs. Day 7 observed 2/9 pigs (N343) and 1/10 pigs (DK15540 p20) IFA positive for Lawsonia antibodies. On day 14, 2/9 pigs were IFA positive in N343 treatment group, 1/10 in DK15540 p20 and p60 respectively. Day 21 revealed 1/10 pigs (N343), 4/10 pigs (N101494) and 6/10 pigs (DK15540 p20) were IFA positive while high passage treatment groups (DK15540 p60 and p80) show no detectable seroconversion. Seroconversion to Lawsonia exposure increased in treatment groups receiving low passage L. intracellularis of both the U.S. and EU isolates day 21 of the study.

Fecal Shedding

PCR testing of the feces demonstrated shedding of L. intracellularis beginning on day 14 where 4/9 in the N343,

TABLE 5

| Group | Treatment | No. of Pigs | Titer ($TCID_{50}$/ml) | Serology | Fecal Shedding | PCR | FA | Histology | Gross Lesions | ADWG | Clinical Scores |
| --- | --- | --- | --- | --- | --- | --- | --- | --- | --- | --- | --- |
| 1 | N343 | 9 | 7.4 | 19% | 11% | 0% | 11% | 44% | 1 | 0.61 | 5.23 |
| 2 | N101494 | 10 | 7.1 | 10% | 10% | 10% | 30% | 30% | 1.2 | 0.8 | 5.15 |
| 3 | DK15540p20 | 10 | 7.2 | 18% | 13% | 30% | 10% | 20% | 1.2 | 0.86 | 5.01 |
| 4 | DK15540p60 | 10 | 7.87 | 5% | 0% | 0% | 0% | 10% | 1 | 0.9 | 5 |
| 5 | DK15540p80 | 20 | 8.4 | 0% | 0% | 0% | 0% | 0% | 1 | 1.05 | 5 |
| 6 | Strict Controls | 10 | 0 | 0% | 0% | 0% | 0% | 0% | 1.05 | 0.91 | 5 |

4/10 in the N101494, and 5/10 in the DK15540 p20 low passage animals tested positive. Both high passage treatment and strict control groups were PCR negative for day 14. On day 21, DK15540 p20 treatment group had 1 animal PCR positive while all other treatment and control groups were PCR negative. No evidence of shedding was observed in high passage isolate groups (DK15540 p60 and p80) using PCR throughout the study. PCR positive animals indicating active shedding of Lawsonia in their feces were more significant in the low passage isolate groups (N343, N101494, and DK15540 p20) on day 14 of the study than high passage isolate groups and strict controls (Pearson Chi-square p<0.05).

PCR at Day 21: Ileums and Colons

PCR testing of mucosal scrapings from ileums and colons was performed after necropsy (day 21). Samples that were PCR positive for *L. intracellularis* colonization were (2/10 colons) in N101494 and (2/10 ileums, and 4/10 colons) in DK 15540 p20 low passage isolate groups. All other treatment and control groups were PCR negative in tissues day 21 of the study. Results indicated ileums and colons of pigs in DK15540 p20 were significantly more colonized with *L. intracellularis* compared to all treatment and control groups (*Pearson Chi-square p<0.05).

Histology

Sections of the terminal ileum and colon were collected at necropsy (day 21) and placed in buffered formalin for histological analysis. Presence of intracellular bacteria and crypt hyperplasia was observed in tissues stained with Hematoxylin and Eosin (H&E) and Warthin-Starry silver reagents of 4/9 pigs (N343), 3/10 pigs (N101494), 2/10 pigs (DK15540 p60) and 1/20 pigs (DK15540 p80). Lesion development was confirmed by florescent antibody staining using monoclonal antibodies against *Lawsonia intracellularis* in 1/9 pigs (N343), 3/10 pigs (N101494), and 1/10 pigs (DK15540 p60). FA detected no lesions caused by *Lawsonia* in the colons of all treatment and control groups. FA results indicated significant lesion development in ileums of pigs in N101494 treatment group compared to all treatment and control groups. H&E/silver staining showed significant lesion development associated with PPE in N343 treatment group compared to all treatment and control groups. (Pearson Chi-square p<0.05).

Gross Scores

Ileums and colons were scored at the time of necropsy (day 21) for lesions associated with PPE. Tissues were given a score of 1 for normal appearance (no lesion development), a score of 2 for lesions demonstrating mild thickening, 3 for moderate thickening, and a score of 4 for severe thickening. Strict controls had an average clinical score of 1.05, N343 (1.0), N101494 (1.2), DK15540 p20 (1.2), and DK15540 p60 and p80 (1.0). Average gross lesion scores indicated no statistical difference between control and treatment groups using ANOVA test for multiple comparisons.

Conclusions

Based on the data collected, this study demonstrated that pigs challenged with a low passage dose of N343, N101494, and DK15540 with a $TCID_{50}$ greater than $1 \times 10^7$ bacteria/dose increases the incidence of PPE in these animals. High passage isolates (DK15540 p60 and p80) given to pigs of the same age with a $TCID_{50}$ greater than $1 \times 10^7$ were proven safe and show reduction of colonization and lesion development associated with PPE. This conclusion was based on PCR on the mucosa of the ileum, histopathology, and FA stains of tissue sections.

A reduction of shedding *L. intracellularis* in the feces determined by PCR was evident in high passage isolates compared to low passage isolates. Average daily weight gains calculated for all treatment and control groups support this conclusion by demonstrating positive uniform daily weight gain in groups given the high passage isolate and strict controls compared to groups given low passage isolates especially animals in the N343 treatment group. This observation indicates reduction of weight gains in animals given low passage material which supports adequate and similar grow performance of animals given high passage material with animals receiving no challenge material. Compared to the strict controls, the high passage isolates showed no negative impact on weight gain and overall health based on clinical scores.

EXAMPLE 3

Efficacy and Minimal Protective Titer

Purpose:

The objectives of this study were to determine the minimal protective titer of a vaccine comprising isolate B3903 (lyophilized) (DK 15540, passage 80) ("B3903 (Lyophilized) vaccine" and "B3903 vaccine" are used interchangeably herein) administered by oral drench in pigs 3 weeks of age and to demonstrate efficacy against a virulent heterologous pure culture challenge with low passage *L. intracellularis*, the causative agent of Porcine Proliferative Enteropathy (PPE) in swine.

Materials and Methods:

Test Substance: Attenuated Live Culture of *L. intracellularis*, Isolate B3903

Formulation of B3903 (Lyophilized) Vaccine

DK 15540 isolates were grown continuously for 80 weeks after isolation in McCoy cell suspension. All cultures were harvested via centrifugation at 10,000 RPM for 15 minutes. The McCoy cell culture pellets containing Lawsonia were resuspended in Sucrose-Phosphate-Glutamine (SPG) solution with 10% FBS. Desiccation was performed as described in Example 1, supra. The lyophilized product is reconstituted in water, q.s. ad 2.0 ml, for injections.

Storage of B3903 (Lyophilized) Vaccine

The vaccine was stored at 2° C.-8° C. until ready for use. After resuspension, the vaccine was stored on ice until administration.

Doses of B3903 (Lyophilized) Vaccine
1. High dose (Treatment Group 1): 1×2 mL (6.0 logs/dose) via direct oral drench on day 0 of the study.
2. Medium dose (Treatment Group 2): 1×2 mL (4.9 logs/dose) via direct oral drench on day 0 of the study.
3. Low dose (Treatment Group 3): 1×2 mL (3.8 logs/dose) via direct oral drench on day 0 of the study.

Test Substance: Placebo

A placebo consisting of uninfected McCoy tissue culture cells suspended in DMEM/F12 growth medium fortified with 5% NBS was given to treatment Groups 4 (challenge control) and 5 (negative control) on day 0 of the study. This substance was administered to piglets in treatment Group 4 by direct oral drench and given 1×2 mL of placebo per test animal.

Test Substance: *L. intracellularis* N101494 Virulent Challenge

*L. intracellularis* N101494 was obtained from the intestines of a 12 week old pig from an Indiana farm (U.S. Pat. No. 5,714,375).

Formulation of *L. intracellularis* N101494 Virulent Challenge

*L. intracellularis* challenge material was grown continuously in McCoy cell suspension no more than 30 passes after initial isolation from infected gut tissue. Active cultures (2×3 L) identified as SF 1422 and SF 1423 in addition to (1 L) SF 1421 were grown in McCoy cell suspension for 7 days to 15-30% McCoy cell infection. On the day of challenge (day 21), active cultures were harvested via centrifugation at 10,000 RPM for 15 minutes and cell pellets resuspended in 350 mls total volume with SPG stabilizer. Harvested active culture was pooled with 300 mLs of frozen 10× to 20× concentrated challenge stocks of low passage N101494 at various passages (pass 24 to 27 post isolation).

Storage of *L. intracellularis* N101494 Virulent Challenge

Final formulations ready for challenge were stored at 2° C. to 8° C. or on ice until inoculation.

Pre/Post-Vaccination and Challenge Titers

Results from the $TCID_{50}$ assay verified the amount of live *L. intracellularis* administered to each test animal per dose during vaccination and challenge. The average titers (n=5) of pre and post titrations for the B3903 vaccine and the challenge material (*L. intracellularis* N101494) were as follows in Table 6:

TABLE 6

| Group | Treatment (logs/dose) | Average logs/dose (2 ml) Pre-vaccination ($TCID_{50}$/ml) | Average logs/dose (2 ml) Post-vaccination ($TCID_{50}$/ml) | Total Average logs/dose |
|---|---|---|---|---|
| 1 | B3903 vaccine high dose | 6.07 | 5.89 | 6.0 |
| 2 | B3903 vaccine medium dose | 4.94 | 4.84 | 4.9 |
| 3 | B3903 vaccine low dose | 3.9 | 3.5 | 3.8 |
| 4 | Challenge Controls | 7.85 | 7.57 | 7.71 |

Study Design

Sixty-five healthy *L. intracellularis* negative weaned piglets at 3 weeks of age were randomly divided into 5 treatment groups and housed separately throughout the study. On day 0, treatment Group 1 (15 pigs) received a 2 mL dose (6.0 logs/dose) of B3903 vaccine by direct oral drench. Treatment Group 2 (15 pigs) received 1×2 mL dose of B3903 vaccine titrated at 4.9 logs/dose by direct oral drench. Treatment Group 3 (15 pigs) received 1×2 mL dose of B3903 vaccine titrated at 3.8 logs/dose by direct oral drench.

Treatment Groups 4 and 5 (10 pigs/group) received 1×2 mL dose of placebo by direct oral drench.

On day 21 of the study (3 weeks post vaccination), test pigs in treatment Groups 1-4 received 1×10 mL dose of virulent low passage pure culture *L. intracellularis* heterologous isolate N101494 by gastric gavage.

On day 42 of the study (3 weeks post challenge), all treatment Groups (1-5) were euthanized and necropsied for gross and microscopic lesion analysis for PPE.

Daily health observations were made from study initiation to the day of challenge for each test animal. Clinical health (diarrhea, behavior, and body condition) were scored daily from day of challenge (day 21) to termination of study (day 42). Weights were taken on day of vaccination (day 0), day of challenge (day 21) and on day of study termination (day 42) to calculate average daily weight gains of each treatment group. Fecal shedding of *L. intracellularis* was evaluated by polymerase chain reaction (PCR) by testing fecal swabs (f-PCR) on days 0, 7, 14, 21, 28, 35, and 42 of the study. All animals euthanized at study termination (day 42) were examined for gross and microscopic lesions. Qualitative analysis of bacterial content in tissues was evaluated by PCR (t-PCR) along with histological evaluation for *L. intracellularis* in the ileum, colon, tonsil, and mesenteric lymph node day 42 of the study. Serum was collected on days 0, 7, 14, 21, 28, 35, and 42 of the study. Serum was tested using the indirect florescent antibody test (IFAT) to detect anti-*Lawsonia* antibodies in test animals. Treatment group comparisons were made by data analysis of average daily weight gains post vaccination and post challenge, clinical scores, seroconversion rates (IFAT), colonization (t-PCR), fecal shedding (f-PCR), gross lesion, and microscopic lesion development by immunohistochemistry (IHC).

Results:

Summary of Primary Results

TABLE 7

| Treatment Group | Pigs per Group | Treatment. Group ID (logs/dose) | Average Gross Lesion Scores (ileum) | Average Gross Lesion Scores (colon) | Average Micro-Lesion scores (ileum) | Average Micro-Lesion Scores (colon) |
|---|---|---|---|---|---|---|
| 1 | 15 | B3903 vaccine high dose (6.0) | 1.5 ab | 1.2 a | 0.2 ab | 0.1 a |
| 2 | 15 | B3903 vaccine medium dose (4.9) | 1.2 ab | 1.0 a | 0.4 ab | 0.0 a |
| 3 | 15 | B3903 vaccine low dose (3.8) | 2.5 b | 1.5 b | 1.0 b | 0.3 a |
| 4 | 10 | Challenge Controls | 3.6 c | 2.2 b | 2.4 c | 1.5 b |
| 5 | 10 | Strict Controls | 1.0 a | 1.0 a | 0.0 a | 0.0 a |

*Like letters indicate no significant difference ($p < 0.05$)

Final test results for each treatment group revealed significant gross and microscopic lesion development of the ileum and colon in non-vaccinated, challenge control pigs (Group 4) compared to vaccinated pigs regardless of dose (high, medium, and low) in Groups 1, 2, and 3 ($p<0.05$). Average gross lesion scores of the vaccine-low dose colons were not significantly different than challenge controls. The vaccine-low dose group (Group 3) is the only treatment group that received vaccine and had significant lesion development (gross and microscopic) in comparison to the strict control group which did not receive a vaccination, placebo, or challenge throughout the study.

Clinical Scores

Clinical scores were recorded for each animal daily from day of challenge (day 21) to necropsy (day 42). Clinical scores were calculated to obtain an average daily clinical score reflecting the severity and duration of sickness among treatment groups due to receiving a virulent challenge of *L. intracellularis*. Average clinical scores for each treatment group are summarized in Table 8.

TABLE 8

| Treatment Group | Group Identification | Average Clinical Score |
|---|---|---|
| 1 | B3903 vaccine - high dose | 3.1 a |
| 2 | B3903 vaccine - medium dose | 3.0 a |

TABLE 8-continued

| Treatment Group | Group Identification | Average Clinical Score |
|---|---|---|
| 3 | B3903 vaccine - low dose | 3.0 a |
| 4 | Challenge Control | 3.0 a |
| 5 | Strict Control | 3.0 a |

*Like letters denote no significant differences among average clinical scores from the day of challenge to necropsy ($p < 0.05$).

Statistical analysis of clinical scores was accomplished by reviewing the data in relation to treatment groups receiving average clinical scores using 1-way ANOVA. There was no evidence of significant differences among non-vaccinated, challenge controls and strict controls compared to the high, medium, or low dose vaccine groups.

Average Daily Weight Gains

Average daily weight gains (ADWG) were calculated from the time of vaccine administration (day 0), to challenge administration (day 21), to the termination of the study (day 42). Statistical analysis of weight gain differences (lbs.=pounds) between vaccine-high dose and non-vaccine, challenge control treatment groups revealed evidence of a significant difference from the time of challenge administration to necropsy ($p<0.05$). The weight data is summarized in Table 9.

TABLE 9

| Treatment Group | Group Identification | Average Initial Weight (lbs.) | ADWG (day 0-21) (lbs.) | ADWG (day 21-42) (lbs.) | ADWG Total (lbs.) (Vaccination to Necropsy) |
|---|---|---|---|---|---|
| 1 | B3903 vaccine high dose | 17.8 a | 0.94 a | 1.63 a | 1.29 a |
| 2 | B3903 vaccine medium dose | 17.7 a | 1.00 a | 1.60 ab | 1.30 a |
| 3 | B3903 vaccine low dose | 18.0 a | 0.94 a | 1.48 ab | 1.21 a |
| 4 | Challenge Control | 17.7 a | 0.96 a | 1.45 b | 1.21 a |
| 5 | Strict Control | 17.7 a | 0.94 a | 1.63 ab | 1.28 a |

*Like letters denote no significant differences between treatment groups in ADWGs from day of vaccination to challenge and from day of challenge to necropsy ($p < 0.05$).

Seroconversion (IFAT)

Serum samples were collected weekly from all test animals in each treatment group and tested for presence of anti-*Lawsonia* IgG antibodies on days 0, 7, 14, 21, 28, 35, and 42 of the study. Positive and negative IFAT control samples were 100% accurate in all assays performed in this study. On days 0 through 21 (3 weeks post vaccination), all test animals in each treatment group were IFA negative. On day 28 (1 week post challenge) of the study 1/15 (6.7%) test animals in the vaccine-high dose treatment group were IFA positive while all others tested IFA negative. On day 35 (2 weeks post challenge) of the study, 4/15 (26.7%) pigs in the vaccine-high dose and medium dose treatment groups and 1/10 (10%) pigs in the non-vaccine, challenge control treatment group were IFA positive for *Lawsonia* antibodies. Both vaccine-low dose and strict control treatment groups were IFA negative on day 35. On day 42 (3 weeks post challenge) of the study, 8/10 (80%) pigs in the challenge control group, 6/15 (40%) pigs in the vaccine-medium dose group, 5/15 (33.3%) pigs in the vaccine-low dose group, and 3/15 (20%) pigs in the vaccine-high dose group were IFA positive. The strict control treatment group was IFA negative at study termination (day 42).

Seroconversion data was analyzed using the Chi-square statistic. For results obtained in the strict control treatment group, a chi-square statistic was not computed due to the 100% negative responses found for each test animal throughout the study. In treatment groups receiving a vaccine or placebo, IFAT results were compared using Chi-square statistic with an estimation of exact p-value (Monte-Carlo). Positive IFAT results obtained from challenge groups receiving a virulent pure culture challenge were significantly higher than those receiving vaccine-high dose and vaccine-low dose ($p<0.05$) at day 42 (3 weeks post challenge) of the study.

Fecal Shedding of *L. intracellularis* (PCR)

Fecal swabs were collected weekly from all test animals in each treatment group and tested for the presence of *L. intracellularis* by PCR on days 0, 7, 14, 21, 28, 35, and 42 of the study. Positive and negative DNA extraction and PCR reaction controls were 100% accurate for each assay conducted in this study. All test animals in each treatment group were fecal PCR negative for *L. intracellularis* from day 0 (vaccination) to day 21 (challenge). Pigs in the strict control group remained fecal PCR negative for *L. intracellularis* in their feces throughout the study. Fecal shedding of *L. intracellularis* (fecal PCR positive) was evident in various treatment groups each week after challenge inoculation. These results are summarized in Table 10.

TABLE 10

| Treatment Group | Group Identification | Day 28 (1 week post challenge) | Day 35 (2 weeks post challenge) | Day 42 (3 weeks post challenge) |
|---|---|---|---|---|
| 1 | B3903 vaccine high dose | 0/15 (0%) a | 2/15 (13.3%) a | 0/15 (0%) a |
| 2 | B3903 vaccine Medium dose | 6/15 (40%) ab | 5/15 (33.3%) a | 0/15 (0%) a |
| 3 | B3903 vaccine low dose | 4/15 (26.7%) ab | 8/15 (53.3%) ab | 2/15 (13.3%) ab |
| 4 | Challenge Control | 4/10 (40%) b | 7/10 (70%) b | 4/10 (40%) b |
| 5 | Strict Control | 0/10 (0%) | 0/10 (0%) | 0/10 (0%) |

*Like letters denote no significant difference among treatment groups receiving a challenge ($p < 0.05$).

Statistical analysis using Chi-square statistic with an estimation of the exact p-value (Monte Carlo) compared the positive responses in each vaccine treatment group to the non-vaccine, challenge control group only. Results from the strict control group were withdrawn from group comparisons because each pig was 100% fecal PCR negative for *L. intracellularis* throughout the study. On day 28 (1 week post challenge), pigs receiving a high dose of vaccine had significantly less shedding of *L. intracellularis* than non-vaccinated, challenged pigs ($p=0.017$). On day 35 (2 weeks post challenge), pigs receiving a high dose ($p=0.0024$) and medium dose ($p=0.041$) of vaccine had significantly less shedding of *L. intracellularis* in their feces than non-vaccinated challenged pigs. On day 42 (study termination), again, pigs receiving a high and medium dose of vaccine ($p=0.017$) had significantly less shedding of *L. intracellularis* in their feces compared to the non-vaccinated, challenged pigs. Pigs in the low dose group were not significantly less PCR positive than the challenge controls on any day post challenge.

*L. intracellularis* Tissue Colonization (PCR)

Polymerase Chain Reaction testing of tissue sections of the terminal ileum, colon, tonsil, and mesenteric lymph node were performed after necropsy (day 42 of the study). In the vaccine-high dose group, 1/15 (6.7%) pigs were PCR positive for *L. intracellularis* colonization in the tonsil while all other treatment groups were PCR negative. Ileitis PCR testing of mesenteric lymph tissue revealed 3/10 (30%) pigs in the non-vaccinated, challenge controls were positive for *L. intracellularis* colonization while all other treatment groups were PCR negative. Ileitis PCR testing of mucosal scrapings of the terminal ileum revealed 4/10 (40%) pigs in the challenge controls, 4/15 (26.7%) pigs in the vaccine-low dose group, 2/15 (13.3%) pigs in the vaccine-medium dose group, and 1/15 (6.7%) pigs in the vaccine-high dose group PCR positive for *L. intracellularis* colonization. Ileitis PCR testing of the colon revealed 3/10 (30%) pigs in the challenge controls, 5/15 (33.3%) pigs in the vaccine-low dose group, 1/15 (6.7%) pigs in the vaccine-medium dose group, and 2/15 (13.3%) pigs in the vaccine-high dose group PCR positive for *L. intracellularis* colonization. No evidence of *L. intracellularis* colonization was seen in tissues of the strict control group.

Statistical analysis of Ileitis PCR positive results were compared among treatment groups using Chi-square statistic with Monte Carlo approximation of the exact p-value. Mesenteric lymph node PCR results indicated evidence of a significant difference among non-vaccinated, challenge controls and all treatment groups receiving a vaccine treatment (p=0.054). No statistical significance was evident among treatment groups in *L. intracellularis* colonization in the ileum, colon, or tonsil at day 42 of the study.

Histology (IHC/H&E)

Sections 2 to 4 cm in length of tonsil, mesenteric lymph node, terminal ileum, and colon were collected at necropsy (day 42) and placed in 10% buffered formalin for histological analysis. *Lawsonia intracellularis* was not detected by IHC staining of tonsil sections in all treatment groups at necropsy. The strict control group was negative for *L. intracellularis* by IHC in all tissue samples taken at necropsy. Presence of *L. intracellularis* and microscopic lesions associated with PPE were found in the ileums of 9/10 (90%) pigs of the non-vaccinated, challenge controls, 6/15 (40%) pigs of the vaccine-low dose group, 3/15 (20%) pigs of the vaccine-medium dose group, and 1/15 (6.7%) pigs of the vaccine-high dose group respectively. Microscopic lesions were evident in the colon of 8/10 (80%) pigs in the challenge control group, 3/15 (20%) pigs in the vaccine-low dose group, and 1/15 (6.7%) pigs in the vaccine-high dose group. The vaccine group receiving a medium dose was IHC negative for *L. intracellularis* in the colon. Stained sections of mesenteric lymph node produced only 1/10 (10%) pigs in the challenge control that had *L. intracellularis*. Positive IHC results in sections of the ileum and colon among treatment groups correlated well to the presence of marked crypt hyperplasia demonstrated by H&E methodology.

Statistical analysis of quantitative IHC data was accomplished using 1-way ANOVA and Kruskal-Wallis Rank Sum tests followed by specific contrasts of p-values between the challenge group and strict control groups to each vaccine dosage group. Statistical analysis reveal evidence of a significant lesion development due to *L. intracellularis* in the ileum and colon of the challenge control group compared to vaccinated pigs regardless of dose on day 42 of the study (p<0.001). Statistical significance was not evident in average IHC lesion scores of the ileum and colon in vaccinated animals receiving a high or medium dose of vaccine compared to the strict control treatment group (p>0.05). Pigs receiving a low dose of vaccine had significantly higher mean microscopic lesion scores due to *L. intracellularis* in the ileum compared to the strict control group (p<0.05).

Gross Scores

The ileum and colon of each test animal were scored at the time of necropsy (day 42) for gross lesions associated with PPE. Tissues from test pigs in the strict control were normal, did not contain lesions, and received average lesion scores of 1.1 (ileum) and 1.0 (colon). Tissues of test animals in the non-vaccinated, challenge control group received the highest average gross lesion score for the ileum (3.6) and colon (2.0) among treatment groups. Test pigs in the vaccine-low dose group received average gross lesion scores of 2.5 (ileum) and 1.5 (colon). Vaccine-medium dose test pigs received average gross lesion scores of 1.5 (ileum) and 1.0 (colon). Tissues of the vaccine-high dose group received average gross lesion scores of 1.5 (ileum) and 1.2 (colon).

Statistical analysis of average gross lesion scores among treatment groups was accomplished by using 1-way ANOVA. Average gross lesion scores indicated evidence of a significant difference between ileums in non-vaccinated, challenge control group and vaccine-medium and high dose groups respectively (p<0.001). Evidence of a significant difference was observed among average gross ileum scores of the challenge control compared to the vaccine-low dose group (p<0.01). Average gross lesion scores of the colon were significantly higher in the challenge control group compared to the vaccine-medium and high dose groups respectively (p<0.05). In addition, significant gross lesion development was observed in the ileum of the vaccine-low dose group compared to the strict control group (p<0.001). No evidence of a statistical significance in average gross lesion scores (ileum and colon) were evident in vaccine-medium and high dose groups compared to the strict control treatment group.

CONCLUSIONS

This study demonstrated protection in 3-week-old pigs against PPE was accomplished when given an oral 2 mL dose of B3903 (Lyophilized) vaccine containing a minimum of 4.9 logs of live *L. intracellularis* per dose. Similar if not slightly better protection was evident in the vaccine-high dose treatment group that received 6.0 logs/dose 3 weeks prior to challenge. The low dose vaccine group (3.8 logs/dose) did not indicate adequate protection against a virulent pure culture heterologous challenge compared to the test animals receiving a high or medium dose of the experimental vaccine. Statistical differences were evident among the vaccine-low dose group and non-vaccinated, challenge controls regarding the severity of microscopic lesions in the ileum and colon (p<0.001) and average gross lesion scores of the ileum (p<0.01). However, significant PPE lesions were observed in the ileum (microscopic lesions) and colon (gross lesions) of this group compared to the strict control group that did not receive vaccine or challenge.

In summary, the data from this study demonstrated that: (1) the minimum protective titer of a single oral administration of B3903 (Lyophilized) vaccine to 3 week old pigs is 4.9 logs/dose; (2) B3903 (Lyophilized) vaccine is efficacious against a virulent low passage pure culture *L. intracellularis*, heterologous isolate N101494; and (3) B3903 (Lyophilized) vaccine aids in the reduction of gross and microscopic lesions, tissue colonization, and fecal shedding of *L. intracellularis* in vaccinated pigs compared to non-vaccinated pigs.

What is claimed is:

1. An avirulent isolate of *Lawsonia intracellularis*, wherein said avirulent isolate is *Lawsonia intracellularis* deposit isolate ATCC No. PTA-4926.

2. A vaccine for the immunization of an animal, comprising a pharmaceutically effective amount of the avirulent isolate of *Lawsonia intracellularis* according to claim 1, and a pharmaceutically acceptable carrier.

3. The vaccine according to claim 2 wherein the pharmaceutically effective amount of the avirulent isolate of *Lawsonia intracellularis* is about $10^3$ $TCID_{50}$ to about $10^6$ $TCID_{50}$ per dose.

4. A vaccine for the immunization of an animal, comprising the avirulent isolate of *Lawsonia intracellularis* according to claim 1 and antigenic material from at least one of the following pathogens: *Salmonella* spp., *Erysipelothrix* spp., *Haemophilus* spp., *Mycoplasma* spp., *Leptospira* spp., *Clostridium* spp., *Streptococcus* spp., *Brachyspira* spp., circovirus, porcine reproductive and respiratory syndrome (PRRS) virus, swine influenza virus (SIV), transmissible gastro-enteritis (TGE) virus, parvovirus, or *Escherichia coli*; and a pharmaceutically acceptable carrier.

5. A vaccine for the immunization of an animal, comprising the avirulent isolate of *Lawsonia intracellularis* according to claim 1 and antigenic material from *Salmonella choleraesuis, Eysipelothrix* spp. transmissible gastro-enteritis (TGE) virus, *Escherichia coli, Clostridium* spp., and *Brachyspira* spp.; and a pharmaceutically acceptable carrier.

6. A vaccine for the immunization of an animal, comprising the avirulent isolate of *Lawsonia intracellularis* according to claim 1 and antigenic material from *Salmonella choleraesuis* and *Erysipelothrix* spp.; and a pharmaceutically acceptable carrier.

7. A vaccine for the immunization of an animal, comprising the avirulent isolate of *Lawsonia intracellularis* according to claim 1 and antigenic material from at least one of the following pathogens: *Clostridium* spp., equine influenza virus (EIV), equine herpes virus (EHV), alphavirus, and West Nile virus; and a pharmaceutically acceptable carrier.

* * * * *